(12) United States Patent
Dang et al.

(10) Patent No.: US 11,807,856 B2
(45) Date of Patent: Nov. 7, 2023

(54) **RECOMBINANT *PICHIA PASTORIS* STRAIN AND METHOD FOR PRODUCING ACTIVE PEDIOCIN PA-1**

(71) Applicant: VIET NAM NATIONAL UNIVERSITY HO CHI MINH CITY, Ho Chi Minh (VN)

(72) Inventors: Phuong Thao Thi Dang, Ho Chi Minh (VN); My Trinh Thi Nguyen, Hue (VN); Nghia Hieu Nguyen, Kien Giang (VN); Thuoc Linh Tran, Ho Chi Minh (VN); Anh Thu Pham Nguyen, Lam Dong (VN)

(73) Assignee: VIET NAM NATIONAL UNIVERSITY HO CHI MINH CITY, Thu Duc (VN)

( * ) Notice: Subject to any disclaimer, the term of this patent is extended or adjusted under 35 U.S.C. 154(b) by 0 days.

(21) Appl. No.: 16/237,684

(22) Filed: Jan. 1, 2019

(65) Prior Publication Data

US 2021/0062200 A1    Mar. 4, 2021

(51) Int. Cl.
*C12N 15/81*    (2006.01)
*C07K 1/18*    (2006.01)
*C07K 1/20*    (2006.01)
*C07K 14/195*    (2006.01)

(52) U.S. Cl.
CPC .............. *C12N 15/815* (2013.01); *C07K 1/18* (2013.01); *C07K 1/20* (2013.01); *C07K 14/195* (2013.01)

(58) Field of Classification Search
None
See application file for complete search history.

(56) References Cited

PUBLICATIONS

Schoeman, H., et al. 1999 Yeast 15: 647-656. (Year: 1999).*
Gutiérrez, J., et al. 2005 Antimicrobial Agents and Chemotherapy 49(7): 3004-3008. (Year: 2005).*
Garsa, A.K., et al. 2014 Probiotics & Antimicro Prot 6: 47-58. (Year: 2014).*
Sigma Aldrich Introduction to Yeast Media Technical Document: 5 pages; obtained from the internet on Feb. 9, 2021. (Year: 2021).*
Invitrogen Pichia Pastoris Expression System 2006: 4 pages. (Year: 2006).*
Beaulieu, L, et al. 2005 Protein Expression and Purification 43: 111-125. (Year: 2005).*
Marugg, J.D., et al. 1992 Applied and Environmental Microbiology 58(8): 2360-2367. (Year: 1992).*

* cited by examiner

*Primary Examiner* — Marsha Tsay (57) ABSTRACT

A recombinant *Pichia pastoris* strain which is genetically modified for highly expressing pediocin PA-1 and secreted into a medium so that the pediocin PA-1 is easily collected and purified from the culture medium. The obtained pediocin PA-1 has specific antimicrobial activities against *Listeria monocytogenes* ATCC 13932 and several other bacteria strains.

19 Claims, 8 Drawing Sheets

Specification includes a Sequence Listing.

SEQ ID NO:1  Pichia pastoris

| aaa | tat | tat | ggt | aat | ggt | gtt | act | tgt | ggt | aaa | cat | tct | tgt | tct | gtt | 48 |
| Lys | Tyr | Tyr | Gly | Asn | Gly | Val | Thr | Cys | Gly | Lys | His | Ser | Cys | Ser | Val | |
| 1 | | | | 5 | | | | | 10 | | | | | 15 | | |

| gat | tgg | ggt | aaa | gct | act | act | tgt | att | att | aat | aat | ggt | gct | atg | gct | 96 |
| Asp | Trp | Gly | Lys | Ala | Thr | Thr | Cys | Ile | Ile | Asn | Asn | Gly | Ala | Met | Ala | |
| | | | 20 | | | | | 25 | | | | | 30 | | | |

| tgg | gct | act | ggt | ggt | cat | caa | ggt | aat | cat | aaa | tgt | taa | | | | 135 |
| Trp | Ala | Thr | Gly | Gly | His | Gln | Gly | Asn | His | Lys | Cys | | | | | |
| | | | 35 | | | | | 40 | | | | | | | | |

SEQ ID NO:2  forward primer XhoIF tga ctc gag aaa aga aaa tat tat ggt aat ggtg        34

SEQ ID NO:3  reverse primer Not1R gatgcggccg ctcattaaca tttatgatta ccttgatga        39

SEQ ID NO:4  forward primer AOXF gactggttcc aattgacaag c        21

SEQ ID NO:5  reverse primer AOXR gcaaatggca ttctga        16

SEQUENCE LISTING

```
<160> NUMBER OF SEQ ID NOS: 5

<210> SEQ ID NO 1
<211> LENGTH: 135
<212> TYPE: DNA
<213> ORGANISM: Pichia pastoris
<220> FEATURE:
<223> OTHER INFORMATION: PEDIOCIN PA-1
<220> FEATURE:
<221> NAME/KEY: CDS
<222> LOCATION: (1)..(132)

<400> SEQUENCE: 1 aaa tat tat ggt aat ggt gtt act tgt ggt aaa cat tct tgt tct gtt      48
Lys Tyr Tyr Gly Asn Gly Val Thr Cys Gly Lys His Ser Cys Ser Val
1               5                   10                  15
```

```
gat tgg ggt aaa gct act act tgt att att aat aat ggt gct atg gct        96
Asp Trp Gly Lys Ala Thr Thr Cys Ile Ile Asn Asn Gly Ala Met Ala
            20                  25                  30 tgg gct act ggt ggt cat caa ggt aat cat aaa tgt taa                   135
Trp Ala Thr Gly Gly His Gln Gly Asn His Lys Cys
        35                  40

<210> SEQ ID NO 2
<211> LENGTH: 34
<212> TYPE: DNA
<213> ORGANISM: Artificial Sequence
<220> FEATURE:
<223> OTHER INFORMATION: forward primer XhoIF

<400> SEQUENCE: 2 tga ctc gag aaa aga aaa tat tat ggt aat ggtg                           34

<210> SEQ ID NO 3
<211> LENGTH: 39
<212> TYPE: DNA
<213> ORGANISM: Artificial Sequence
<220> FEATURE:
<223> OTHER INFORMATION: reverse primer NotlR

<400> SEQUENCE: 3
gatgcggccg ctcattaaca tttatgatta ccttgatga                             39

<210> SEQ ID NO 4
<211> LENGTH: 21
<212> TYPE: DNA
<213> ORGANISM: Artificial Sequence
<220> FEATURE:
<223> OTHER INFORMATION: forward primer AOXF

<400> SEQUENCE: 4
gactggttcc aattgacaag c                                                21

<210> SEQ ID NO 5
<211> LENGTH: 16
<212> TYPE: DNA
<213> ORGANISM: Artificial Sequence
<220> FEATURE:
<223> OTHER INFORMATION: reverse primer AOXR

<400> SEQUENCE: 5
gcaaatggca ttctga                                                      16
```

RECOMBINANT *PICHIA PASTORIS* STRAIN AND METHOD FOR PRODUCING ACTIVE PEDIOCIN PA-1

FIELD OF THE INVENTION

The present invention relates to the field of recombinant pediocin PA-1 production. More particularly, this invention relates to the production of pediocin PA-1 from a yeast strain.

BACKGROUND OF INVENTION

Bacteriocins are pediocins that are produced by bacteria. More specifically, they are peptides or proteins which are produced by both Gram-positive and Gram-negative bacteria. Baceteriocins possess antimicrobial activities against related or non-related species to the producing strain (Line et al., 2008; Nazef et al., 2008; Messaoudi et al., 2011). Due to their antimicrobial activities against a variety of pathogens and food spoilers, bacteriocins have significant potential for replacing antibiotics in food preservation and in pharmaceutical industry.

Since the first bacteriocin, colicin V, was discovered by Gratia in 1925 (Gratia and Fredericq, 1946), various bacteriocins have been found and extensively studied. Pediocin PA-1, produced by *Pediococcus acidilactici* PAC1.0, is one of the class IIa bacteriocins. It is a 4.6 kDa peptide with 44 amino acids and has the isoelectric point (pp of 8.6-10 (Henderson et al., 1992; Venema et al., 1997). Similar to the other members of class IIa bacteriocins, pediocin PA-1 is stable at high temperature. It was found to remain its full activities after being treated at 100° C. for 60 minutes. However, when placed at 121° C., the antimicrobial activities gradually reduced after 15 minutes and completely disappeared after 20 minutes treatment (Mandal et al., 2014). It was also reported that pediocin PA-1 was stable at the pH levels of 2-8 for at least 2 hours (Mandal et al., 2014).

Importantly, pediocin PA-1 displays activities against a wide spectrum of Gram-positive bacteria, including Lactobacilli, *Leuconostoc, Brochothrix thermosphacta*, Probionibacteria, Bacilli, Enterococci, Staphylococci, *Listeria clostridia, Listeria monocytogenes, Listeria innocua* (Bactibase—BAC083) (Henderson et al., 1992). In addition to the antimicrobial activities, pediocin PA-1 inhibited the growth of the human lung carcinoma cell line A-549 and the human colon adenocarcinoma cell line DLD-1 (Beaulieu, 2005).

Currently, pediocin PA-1 from *P. acidilactici* has been marketed under the commercial name Alta™ 2341 that can be used as a food ingredient to extend the shelf-life of a variety of foods and particularly to inhibit the growth of *Listeria monocytogenes* in some kinds of meat products (Chen et al., 2005). Despite having a remarkable and promising potential for applications in food preservation and pharmaceutical industry, pediocin PA-1 is currently provided at high price due to its ineffective and high-cost production processes.

Therefore, besides obtaining from the native producing strain *P. acidilactici*, several other approaches using other expression systems such as *Escherichia coli, Saccharomyces cerevisiae*, and *Pichia pastoris* to produce recombinant pediocin PA-1 have been developed in attempts to reduce the cost of this product.

Halami and Chandrashekar (2007) succeeded in using the *E. coli* BL21(DE3) system to express pediocin PA-1 as inclusion bodies. The recombinant pediocin PA-1 was denatured, refolded, and purified with the final yield of 3 mg/l, and exhibited biological activities against *Listeria monocytogenes* V7.

In a study of Moon et al. (2006), *E. coli* M15 was used to express pediocin PA-1 fused with dihydrofolate reductase (DHFR). The final yield after purification by ultrafiltration was 8.3 mg/l and the antimicrobial activity was detected against *L. plantarum* NCDO 955.

Schoeman et al. (1999) successfully used *Saccharomyces cerevisiae* to express and secrete pediocin PA-1 into the medium. Although the recombinant pediocin PA-1 showed antimicrobial activity against *Listeria monocytogenes* B73, it was present at relatively low levels in the culture medium.

Beaulieu et al. (2015) used the methylotrophic yeast *Pichia pastoris* to express heterologous pediocin PA-1 and a significantly high concentration of extracellular recombinant pediocin (74 µg/ml) was obtained. However, the recombinant pediocin PA-1 appeared as a mixture of three main forms with different molecular weights and showed no biological activity against the indicated bacterial strain *P. pentosaceus* due to the presence of collagen-like materials.

Since then, no further study regarding the production of pediocin PA-1 from *Pichia pastoris* was reported. Therefore, so far, although *Pichia pastoris* was shown to be a promising candidate for the heterologous production of recombinant protein due to the ability to efficiently express and secrete it into a culture medium, the generation of pediocin PA-1 having antimicrobial activities from the *Pichia Pastoris* strain has not been succeeded. Thus, there exists a market demand to develop pediocin PA-1 from *Pichia pastoris*, but so far no one is able to fulfil this long-felt need.

Therefore, what is needed is a pediocin PA-1 that is easy and inexpensive to produce.

Furthermore, what is needed is a pediocin PA-1 that is produced by a yeast strain instead of bacteria.

Yet, what is needed is a pediocin PA-1 that has antimicrobial activities against at least 7 different bacteria strains.

Yet, what is needed is a pediocin PA-1 that is stable at extremely high temperature and pH level, thus potentially useful in food preservation and pharmaceutical applications.

The present invention provides solutions to the above needs and successfully produces pediocin PA-1 from a yeast strain *Pichia pastoris*.

BRIEF SUMMARY OF THE INVENTION

Accordingly, an object of the present invention is to use the *Pichia pastoris* system for the expression of active pediocin PA-1: The integrative vector pPICZαA carrying the α-factor secretion signal sequence was also used to facilitate the secretion of recombinant protein; gene coding for pediocin PA-1 was inserted into vector pPICZαA under the control of AOX1 promoter and in-frame with the α-factor secretion sequence; after that, the expression cassette was then integrated into the yeast genome at AOX1 region to promote the stable expression of pediocin PA-1; with AOX1 promoter, *Pichia pastoris* has capacity to utilize methanol not only as a source of carbon and energy but also as a factor to induce the expression of target proteins; as a result, pediocin PA-1 can be expressed and secreted into the culture medium when induced by methanol.

Another object of the present invention is to generate a DNA sequence encoding pediocin PA-1 and a recombinant *Pichia pastoris* strain that can express active pediocin PA-1 and secrete it into the culture medium.

Another object of the present invention is to create a recombinant yeast such as *Pichia pastoris* strain that can produce pediocin PA-1 having antimicrobial activities against *Listeria monocytogenes* ATCC 13932 and at least 7 different bacterial strains such as *Listeria innocua, Listeria monocytogenes* VSVTCC, *Vibrio parahaemolyticus, Enterococcus faecalis, Streptococcus thermophilus*, and *Lactobacillus plantarum*.

Yet another object of the present invention is to provide specific conditions to efficiently produce pediocin PA-1 from the recombinant *Pichia pastoris* strain and the methods to obtain the purified active pediocin PA-1 from specific culture medium of expressing strain.

Another object of the present invention is to provide a cost-effective and simple method for producing pediocin PA-1 that can maintain antimicrobial activities at high temperatures and at a wide range of pH levels.

These and other advantages of the present invention will no doubt become obvious to those of ordinary skill in the art after having read the following detailed description of the preferred embodiments, which are illustrated in the various drawing Figures.

BRIEF DESCRIPTION OF THE DRAWINGS

The accompanying drawings, which are incorporated in and form a part of this specification, illustrate embodiments of the invention and, together with the description, serve to explain the principles of the invention.

DETAILED DESCRIPTION OF THE INVENTION

Reference will now be made in detail to the preferred embodiments of the invention, examples of which are illustrated in the accompanying drawings. While the invention will be described in conjunction with the preferred embodiments, it will be understood that they are not intended to limit the invention to these embodiments. On the contrary, the invention is intended to cover alternatives, modifications and equivalents, which may be included within the spirit and scope of the invention as defined by the appended claims. Furthermore, in the following detailed description of the present invention, numerous specific details are set forth in order to provide a thorough understanding of the present invention. However, it will be obvious to one of ordinary skill in the art that the present invention may be practiced without these specific details. In other instances, well-known methods, procedures, components, and circuits have not been described in detail so as not to unnecessarily obscure aspects of the present invention.

Figure 1:
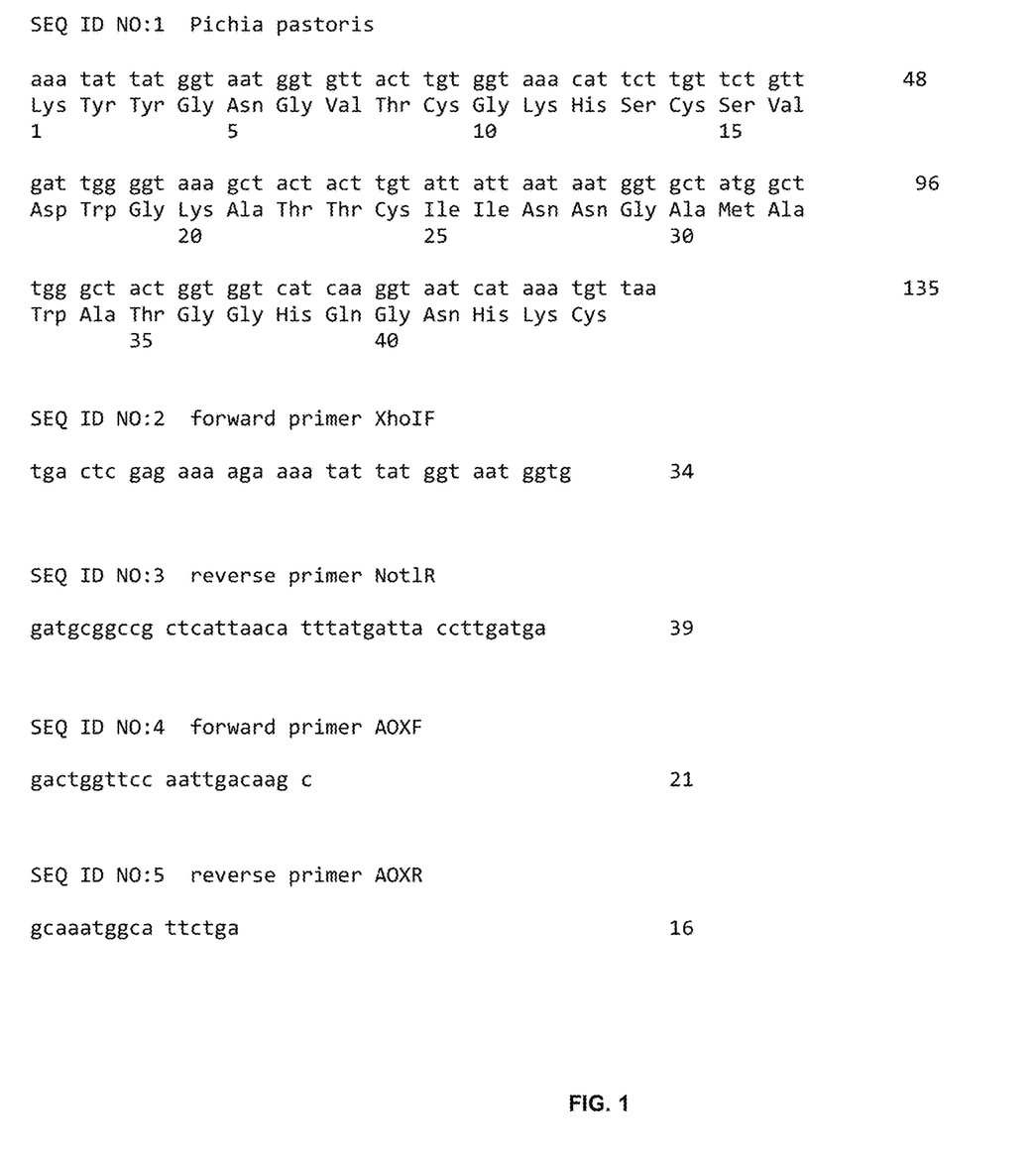
FIG. 1 shows the optimized nucleic acid sequence of gene ped coding for pediocin PA 1 consisting the nucleic acid sequence set forth in SEQ ID NO: 1 and nucleic acid sequences of forward primer XhoIF having the nucleic acid sequence set forth in SEQ ID NO: 2 and reverse primer NotIR having the nucleic acid sequence set forth in SEQ ID NO: 3 and forward primer AOXF having the nucleic acid sequence set forth in SEQ ID NO: 4 and reverse primer AOXR having the nucleic acid sequence set forth in SEQ ID NO: 5 of a promoter AOX1 in accordance with an exemplary embodiment of the present invention.

Now referring to FIG. 1, FIG. 1 shows the coding sequence expressed as SEQ ID NO: 1 of a DNA molecule that encodes pediocin PA-1 which is named as ped. Please see the Sequence Listing. The first aspect of the present invention is a deoxyribonucleic acid (DNA) molecule encoding a pediocin PA-1 from *Pediococcus acidilactici* PAC1.0. The DNA sequence is optimized to match the genetic code of *Pichia pastoris* host cell. In one exemplary embodiment of the present invention, a sample of *Pichia pastoris* strain which is *Pichia pastoris* X33::ped has been deposited with the Agricultural Research Service Culture Collection in Peoria, Illinois, USA on Jun. 21, 2018 under the Budapest Treaty and was assigned accession number NRRL Y-67635. FIG. 1 also shows a Ped forward primer XhoIF having the nucleic acid sequence set forth in SEQ ID NO: 2, which is TGACTCGAGAAAAGAAAATAT-TATGGTAATGGTG; ped reverse primer NotIR having the nucleic acid sequence set forth in SEQ ID NO: 3, which is GATGCGGCCGCTCATTAACATTTATGATTACCTT-GATGA; an AOX1 forward primer AOXF having the nucleic acid sequence set forth in SEQ ID NO: 4, which is GACTGGTTCCAATTGACAAGC; and AOX1 reverse primer AOXR having the nucleic acid sequence set forth in SEQ ID NO: 5, which is GCAAATGGCATTCTGA.

Continuing with FIG. 1, it has been shown that different organisms display different frequencies of synonymous codons in DNA coding and that the heterologous sequence containing rare codons might not be efficiently translated in host cells (Grantham et al., 1980; Nakamura et al., 1999). Therefore, the optimized DNA sequence encoding pediocin PA-1 of the present invention is a manmade DNA sequence in which the ped is successfully inserted into a yeast strain, particularly *Pichia pastoris*.

Figure 2:
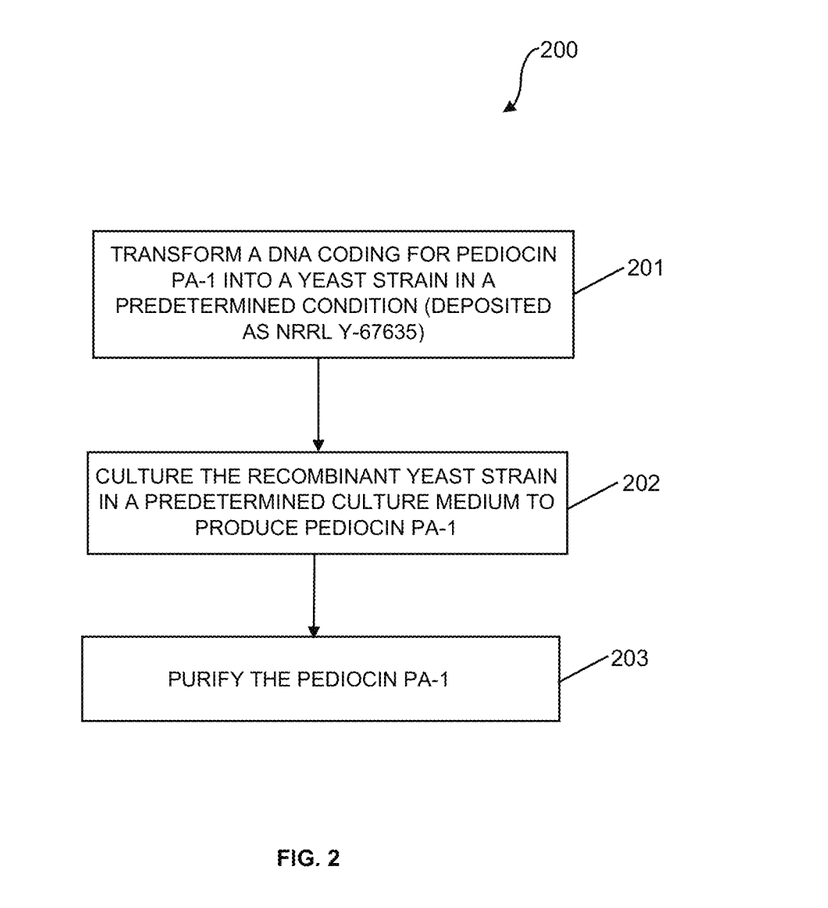
FIG. 2 illustrates a method of producing pediocin PA-1 from a yeast strain such as *Pichia pastoris* in accordance with an exemplary embodiment of the present invention.

Referring now to FIG. 2, in another aspect of the present invention, a method 200 of producing a pediocin PA-1 from a yeast strain described in FIG. 1 is illustrated. In many embodiments of the present invention, method 200 includes a transformation of a DNA gene coding for pediocin PA-1 into a yeast strain in preset conditions conducive to produce the recombinant yeast strain, culturing the recombinant yeast strain in a preset culture medium conducive to producing the pediocin PA-1, and purifying the produced pediocin PA-1 from the preset culture medium of recombinant *Pichia pastoris*.

At step 201, a DNA gene coding for pediocin PA-1, also known as ped, is transformed into a yeast strain. An expression vector used to transform the ped into a *Pichia pastoris* strain contains:
  (a) An origin of replication recognized by *Escherichia coli* cells.
  (b) Sequences encoding selectable markers.
  (c) An expression cassette containing the ped sequence fused with a secretion signal sequence flanked by a *Pichia pastoris*-recognized promoter and terminator.

The expression vector has been constructed by inserting the ped sequence into the vector pPICZαA. In this construction, a promoter AOX1 has been used to facilitate the expression of pediocin PA-1 in the presence of methanol.

An important part of the present invention is a recombinant *Pichia pastoris* strain having ability to produce active pediocin PA-1. In an exemplary implementation of step 201, the recombinant strain is constructed by transforming the above vector into *Pichia pastoris* X33 strain. In cells, the expression cassette is inserted into AOX1 promoter in the genome by homologous recombination to enable the stable expression of pediocin PA-1.

After transformation, the Mut$^s$ or Mut$^+$ phenotype can be obtained if the expression cassette is integrated into the genome with or without the replacement of the AOX1 native gene, respectively. However, only the Mut$^+$ phenotype is chosen in this invention due to the ability of using methanol as the primary carbon source. Thus, the recombinant *Pichia pastoris* cells can produce pediocin PA-1 when methanol is added into the culture medium. A preferred sample of *Pichia pastoris* strain according to the present invention is *Pichia pastoris* X33::ped, which has been deposited with the Agricultural Research Service Culture Collection in Peoria, Illinois, USA on Jun. 21, 2018 under the Budapest Treaty and was assigned accession number NRRL Y-67635.

At step 202, pediocin PA-1 is produced by culturing the above-described *Pichia pastoris* strain in a preset culture medium conducive to produce the pediocin PA-1 have the above-described characteristics. In one exemplary embodiment, step 202 was performed in two different preset culture media in the following sub steps:
  (1) The *Pichia pastoris* strain is culture in a growth medium contains glycerol or sugar as the carbon source and appropriate salt composition containing essential elements including, but not limited to, potassium (K), phosphor (P), a Sulfur (S), Calcium (Ca), Magnesium (Mg), Arsenic (As), Chromium (Cr), Fluorine (F), Iodine (I), Cobalt (Co), Copper (Cu), Manganese (Mn), Molybdenum (Mo), Selenium (Se), Vanadium (V), Zinc (Zn), and tin (Sn) at 25-37° C. with agitation and oxygenation until the end of log phase.
  (2) The culture is fed with medium similar to that described in step (1) but methanol is used as the carbon source instead of glycerol or sugar at 25-37° C. with agitation and oxygenation.

Step (1) represents the growing phase resulting in a vast amount of cell whereas step (ii) is the induction phase, in which the pediocin PA-1 is produced.

In the above processes, the preferred medium in step (1) contains 10 g/L yeast extract, 20 g/L peptone, 13.4 g/L yeast nitrogen base without amino acids, 0.4 mg/L biotin, 1% glycerol, and 100 mM potassium phosphate, pH 6.0; and the preferred medium in step (ii) contains 10 g/L yeast extract, 20 g/L peptone, 13.4 g/L yeast nitrogen base without amino acids, 0.4 mg/L biotin, 0.5% methanol, and 100 mM potassium phosphate, pH 6.0.

At step 203, the pediocin PA-1 from the culture medium is purified from the culture medium of recombinant *Pichia pastoris*. In one exemplary implementation of step 203, pediocin PA-1 can be purified by the cation exchange chromatography.

The cation exchange chromatography method further comprises the following steps:
  (a) using centrifugation to eliminate cells from the culture medium,
  (b) diluting the culture medium at least 4 times by the binding buffer,
  (c) purifying the supernatant by a cation exchange chromatography, in which the binding buffer preferably contains $CH_3COONH_4$ 25 mM, pH 4 and the target peptide is eluted by increasing the concentration of NaCl in the buffer.

In another exemplary embodiment of step 203, pediocin PA-1 is purified by the hydrophobic interaction chromatography.

The hydrophobic interaction chromatography method further comprises the following steps:
  (a) using centrifugation to eliminate cells from the culture medium,
  (b) supplementing ammonium sulphate into the culture medium to the final concentration of 1 M,
  (c) purifying the supernatant by a hydrophobic interaction chromatography, in which the binding buffer preferably contains $Na_2HPO_4$ 50 mM, $(NH_4)_2SO_4$ 1M, pH 7 and the target peptide is eluted by decreasing the concentration of ammonium sulphate salt in the buffer.

After step 203 has completed, the purified pediocin PA-1 has antimicrobial activities against some target bacteria strains. The target bacteria strains of the recombinant pediocin PA-1 may include, but are not limited to, *Listeria monocytogenes* ATCC 13932, *Listeria innocua*, *Listeria monocytogenes* VSVTCC, *Vibrio parahaemolyticus*, *Enterococcus faecalis*, *Streptococcus thermophilus*, and *Lactobacillus plantarum*.

In addition, the activity of purified pediocin PA-1 is stable at high temperature (at least 60 minutes at 100° C. or at lower temperature and at least 20 minutes at 121° C.) and at wide pH range (at least 60 minutes at pH 1-pH 12). Temperature and pH stability are two important characteristics of food preservatives, because high temperature as well as wide range of pH are usually subjected in food processing.

EXAMPLES

The present invention is further defined in the following examples. It should be understood that these examples, while indicating preferred embodiments of the invention, are given by way of illustration only. From the above discussion and these examples, one skilled in the art can ascertain the essential characteristics of this invention, and without departing from the spirit and scope thereof, can make various changes and modifications of the invention to adapt it to various usages and conditions. The notation below of w/v refers to the weight of the active ingredient in grams in 100 mL of solution.

The meaning of abbreviations is as follows: "g/L" means gram per liter, "µg/ml" means micro grams per milliliters, "LB Agar" means Luria-Bertani (LB) broth with Agar, which is the most widely used medium for the growth of bacteria, "YDP" means Yeast Extract Pepton Dextrose, "μL" means microliters, "μg" means micrograms, "kV" means kilo volts, "μF" means micro Farads, "BMGY" means Buffered Glycerol Complex Medium, "rpm" means rounds per minutes, and "BMMY" means Buffered Methanol Complex Medium, "TSB" means Tryptic Soy Broth, a nutritious medium that supports the growth of a wide variety of microorganisms, "AU" means Arbitrary Unit, "M" means mols.

Example 1: Construction of pPICZαA-Ped Expression Vector

Figure 3:
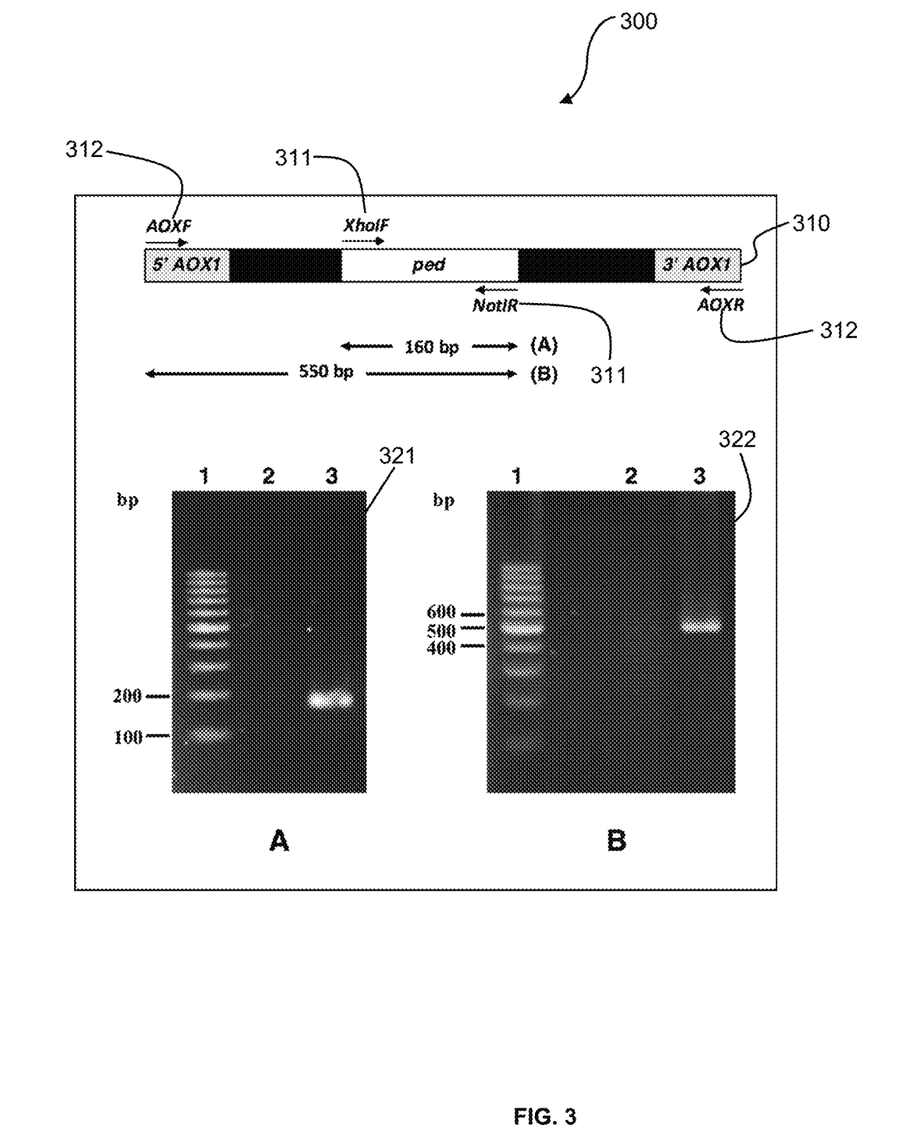
FIG. 3 shows the results of PCR analysis of recombinant vector pPICzαA-ped using the primer pairs XhoIF/NotIR (A) and AOXF/NotIR (B) in accordance with an exemplary embodiment of the present invention.

Now referring to FIG. 3, a graph 300 showing the results of PCR analysis of a recombinant vector pPlCZαA-ped 310 using primer pairs XhoIF/NotIR 311 (A) and AOXF/NotIR 312 (B) are illustrated. The *E. coli* DH5α strain (F−, φ80lacZΔM15, recA1, endA1, hsdR17 (rk−, mk+), phoA, supE44, λ−, thi-1, gyrA96, relA1) and the plasmid pPICZαA were used to construct pPICZαA-ped 310 expression vector. *E. coli* cells were grown in low salt Luria-Bertani (LB) broth (10 g/L tryptone, 5 g/L yeast extract, and 0.5 g/L NaCl). Primers for the Polymerase Chain Reaction (PCR) are shown as follows:

Ped forward primer XhoIF having the nucleic acid sequence set forth in SEQ ID NO: 2 which is: TGACTCGAGAAAAGAAAATAT-TATGGTAATGGTG.

Ped reverse primer NotIR having the nucleic acid sequence set forth in SEQ ID NO: 3 which is: GATGCGGCCGCTCATTAACATTTATGAT-TACCTTGATGA.

AOX1 forward primer AOXF having the nucleic acid sequence set forth in SEQ ID NO: 4 which is: GACTGGTTCCAATTGACAAGC.

AOX1 reverse primer AOXR having the nucleic acid sequence set forth in SEQ ID NO: 5 which is: GCAAATGGCATTCTGA.

The ped gene was amplified by PCR using primer pair XhoIF/NotIR 311. The amplicon was then inserted into plasmid pPICZαA at XhoI/NotI site 311 and in-frame with the α-factor secretion sequence in the plasmid. The recombinant plasmid, named pPICZαA-ped 310, was transformed into *E. coli* cells. The transformants were selected on LB agar medium supplemented with 30 μg/ml zeocin.

Referring again to FIG. 3, the insertion of expression cassette in recombinant vector was confirmed by PCR and DNA sequencing. As a result, two bands 321 and 322 corresponding to products from PCR using two primer pairs XhoIF/NotIR and AOXF/NotIR 312 were detected with correct sizes. Additionally, the DNA sequencing showed that the inserted sequence totally matched to the designed sequence. These data indicate that we succeeded in constructing plasmid pPICZαA-ped 310.

Example 2: Construction of the Recombinant *Pichia pastoris* X33::Ped

Continuing with FIG. 3, to construct the recombinant yeast strain, 10 μg recombinant vector pPICZαA-ped 310 was linearized using SacI restriction endonuclease. After that, 0.5 μg linearized vectors were transformed into 40 μl competent *Pichia pastoris* cells by electroporation at 1.5 kV, 25 μF in 5 mS to construct the recombinant yeast strain *Pichia pastoris* X33::ped. Transformed yeast cells were screened by plating on solid YPD medium containing 100 μg/ml zeocin and incubated for 3-4 days at 30° C.

The presence of ped gene in the genome of obtained colonies was confirmed by PCR with primer pair XhoIF/AOXR. The Mut⁺ phenotype was determined by PCR with primers AOXF/AOXR. From 10 randomly selected clones grown on YPD medium containing 100 μg/ml zeocin, 3 clones having Mut⁺ phenotype were detected. All of them could grow on both solid minimal dextrose (13.4 g/L yeast nitrogen base and 20 g/L D-Glucose) and minimal methanol (13.4 g/L yeast nitrogen base and 0.5% methanol) media.

Example 3: Production of Pediocin PA-1

Figure 4:
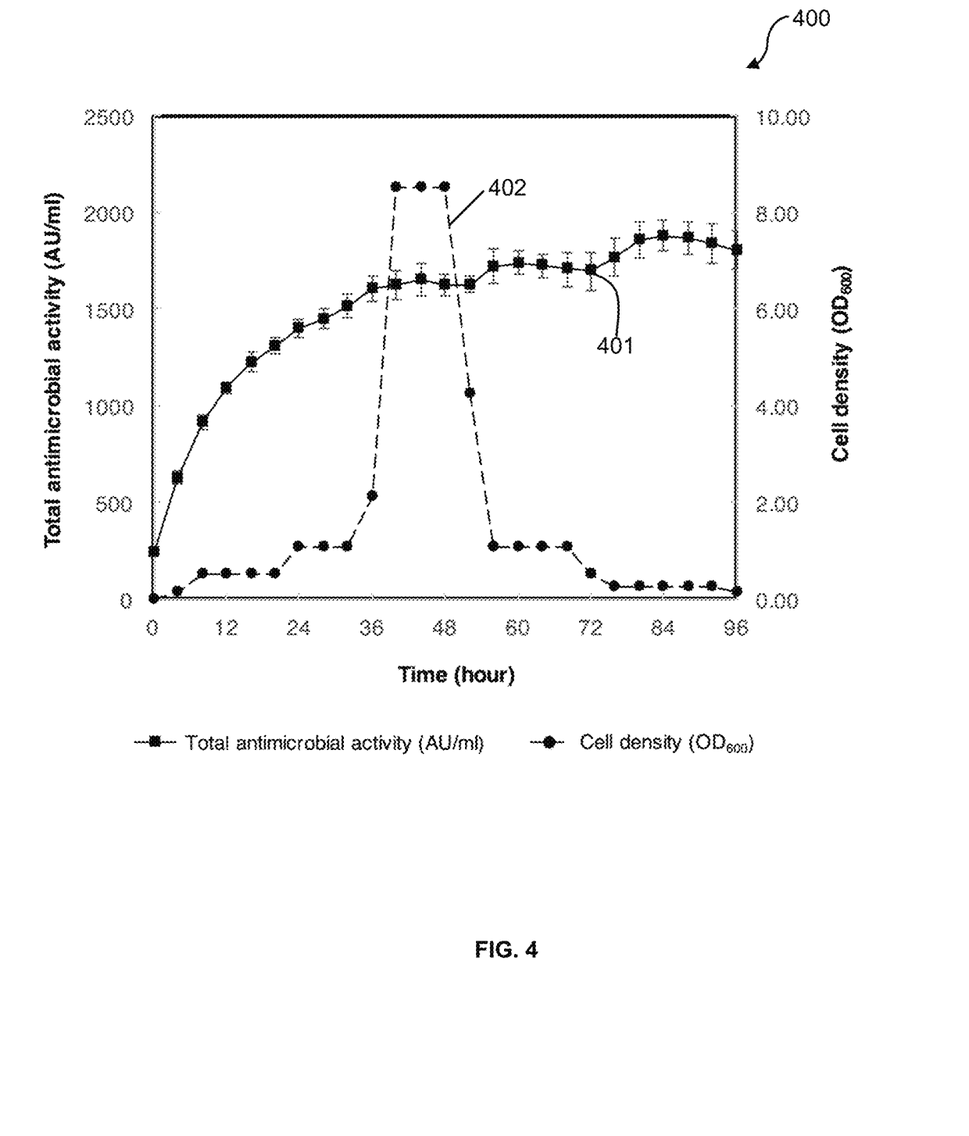
FIG. 4 shows the growth curve of *Pichia pastoris* X33:: ped and antimicrobial activity (AU/ml) curve of culture medium against *Listeria monocytogenes* ATCC13932 after 96 hours of cultivation in accordance with an exemplary embodiment of the present invention.

Referring next to FIG. 4, a graph 400 shows the growth curve of *Pichia pastoris* X33::ped 401 and antimicrobial activity (AU/ml) 402 of culture medium against *Listeria monocytogenes* ATCC13932 after 96 hours of cultivation. To achieve the antimicrobial activity of pediocin PA-1 produced by method 200 of the present invention, the production of pediocin PA-1 were performed in accordance with step 202. *Pichia pastoris* X33::ped cells were pre-cultured in 5-10 ml YPD medium containing 100-200 μg/ml zeocin. The overnight pre-culture was then transferred into 50 ml Buffered Glycerol Complex Medium (BMGY) medium and cultured for 16-20 hours. After that, cells were collected by centrifugation at 5000 rpm, 10° C. for 7 minutes and resuspended in 100-200 ml BMMY medium with the initial $OD_{600}$=1.0-2.0. Cells were cultured further at 25-30° C. with shaking for 72-96 hours. During cultivation, 0.5-1% ethanol was added every 12-24 hours. Aliquots of culture medium were withdrawn every 4 hours to examine the expression of active pediocin PA-1 by antimicrobial assay using agar diffusion test according to Barefoot and Klaenhammer (1983).

In this test, the indicator strain *Listeria monocytogenes* ATCC 13932 were pre-cultured and diluted by TSB medium to $OD_{600}$=0.1. The mixture of 5 ml TSB, 0.8% agar, and 100 μl diluted indicator cells were prepared and poured onto a TSB agar plate.

The cultured medium of *Pichia pastoris* X33::ped was diluted by two-fold dilution method and used for the agar diffusion test. Wells were created in the solidify agar plate with a diameter of 6 mm and filled with 60 μL of samples. The tested plates were cooled at 4° C. for 15 min and then incubated at 37° C.

The diameter of the inhibition zone was measured after 4-5 hours incubation and the inhibition zone with diameter 2 mm (not included diameter of the well) was interpreted as a positive result (Navratilova et al., 2014).

The total antimicrobial activity of a protein/peptide displayed in arbitrary units per ml (AU/ml) was calculated using the following formula:

$$\text{Total antimicrobial activities (AU/ml)}=(2^n \times 1000)/V$$

Wherein, n is the highest dilution fold which yields an inhibition zone with diameter≥2 mm, and V is the volume (μl) of the sample filled in each well.

As shown in FIG. 4, the activity of pediocin PA-1 in culture medium of *Pichia pastoris* X33::ped was detected after 4 hours cultivation in BMMY medium and still remained after 96 hours cultivation. In addition, the highest amounts of pediocin PA-1 could be obtained after 40-48 hours cultivation with the total antimicrobial activity of 2133 AU/ml.

Example 4: Pediocin PA-1 Purification

After 96 hours of incubation, cells were removed and the culture medium of *Pichia pastoris* X33::ped strain was used for pediocin PA-1 purification using cation exchange and hydrophobic interaction chromatography methods.

For cation exchange chromatography, the culture medium was diluted 4 times by buffer A containing ammonium acetate ($CH_3COONH_4$) 25 mM pH 4 and loaded into a 1 ml SP FF column (GE Healthcare Life Sciences) at 1 ml/min. After that, the column was washed with 5 ml buffer A and then, the pediocin PA-1 was eluted by increasing the concentrations of sodium chloride (NaCl) to 0.1-1M in buffer A. For hydrophobic interaction chromatography, the culture medium was supplemented with Ammonium Sulphate to the final concentration of 1M and adjusted to pH 7. Samples were applied at 0.5 ml/min into a 1 ml SP-phenyl column (GE Healthcare Life Sciences) which was equilibrated with buffer B containing Natrium phosphate ($Na_2HPO_4$ 50 mM, Ammonium Sulphate $(NH_4)_2SO_4$ 1M, pH 7), followed by washing the column with 5 ml buffer B. Pediocin was eluted by applying buffer C containing sodium phosphate dibasic ($Na_2HPO_4$ 50 mM, pH 7). The presence of pediocin PA-1 in the elution fractions was determined by Sodium Dodecyl Sulphate Polyacrylamide Gel Electrophoresis (SDS-PAGE) analysis and by the formation of inhibition zones on SDS-PAGE gels as described by Bhunia et al. (1987). According to this method, the SDS-PAGE was fixed with a solution containing 10% acetic acid and 20% isopropanol for 30 minutes, washed carefully with deionized water overnight, then placed into a sterile petri dish and overlaid with 5 ml soft (Tryptic Soy Broth) TSB-agar medium containing diluted indicator bacteria which was prepared using the same method as in agar diffusion test. The tested plate was incubated at 37° C. until inhibition zones were observed. The activity of pediocin PA-1 was also confirmed by gar diffusion test using *Listeria monocytogenes* as an indicator strain.

Figure 5:
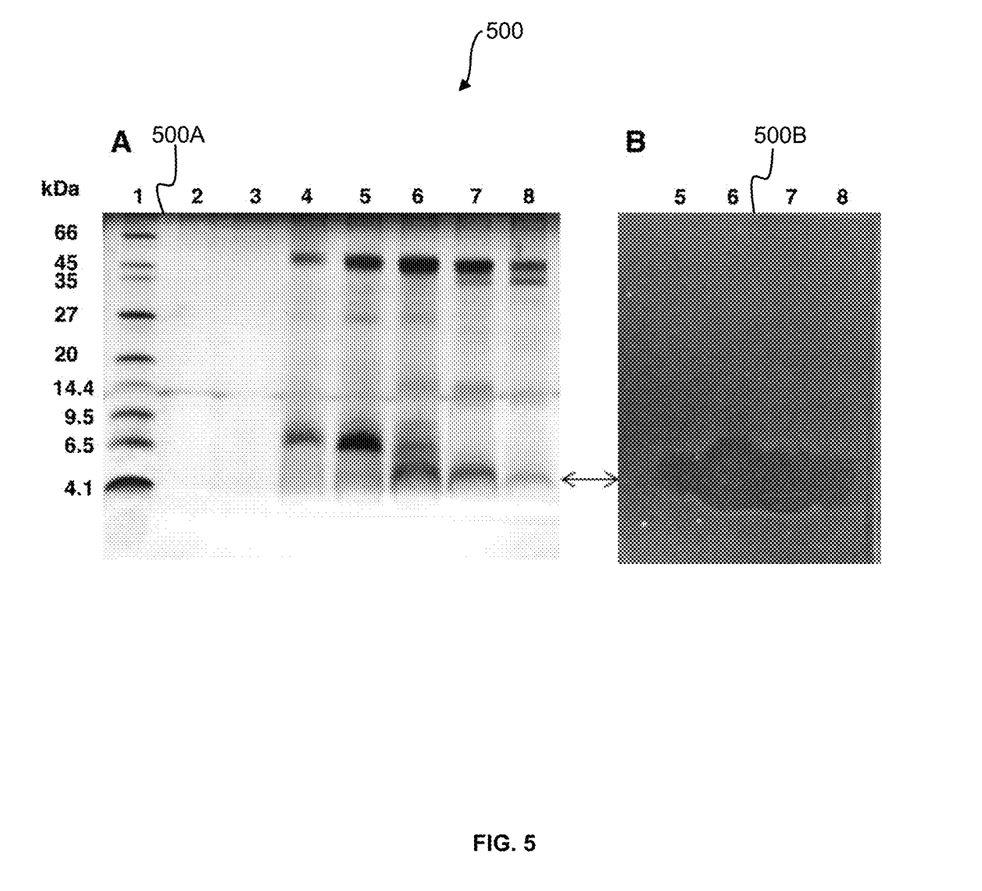
FIG. 5 shows the results of Tricine SDS-PAGE analysis (A) and antimicrobial activity test (B) of pediocin PA-1 purified by cation exchange in accordance with an exemplary embodiment of the present invention.

Referring to FIG. 5, a graph 500A shows the result of Tricine SDS-PAGE analysis (A) and a second graph 500B shows antimicrobial activity test (B) of pediocin PA-1 purified by cation exchange chromatography. Samples are as follows: 1, Weight Marker (Bio Basic Canada Inc.); 2-8, elution fractions at 0.1 M, 0.2 M, 0.3 M, 0.4 M, 0.5 mM, 0.6 M, and 0.7 M NaCl, respectively.

As shown in FIG. 5A, the results in graph 500A showed that from the cation exchange purification, the protein bands with molecular weight of approximately 4.6 kDa (same as that of the native pediocin PA-1) appeared at fractions containing 0.4-0.7 M NaCl. Importantly, in FIG. 5B, graph 500B shows that the clear zones could be observed surrounding these bands, indicating that these elution fractions contained active pediocin PA-1.

Figure 6:
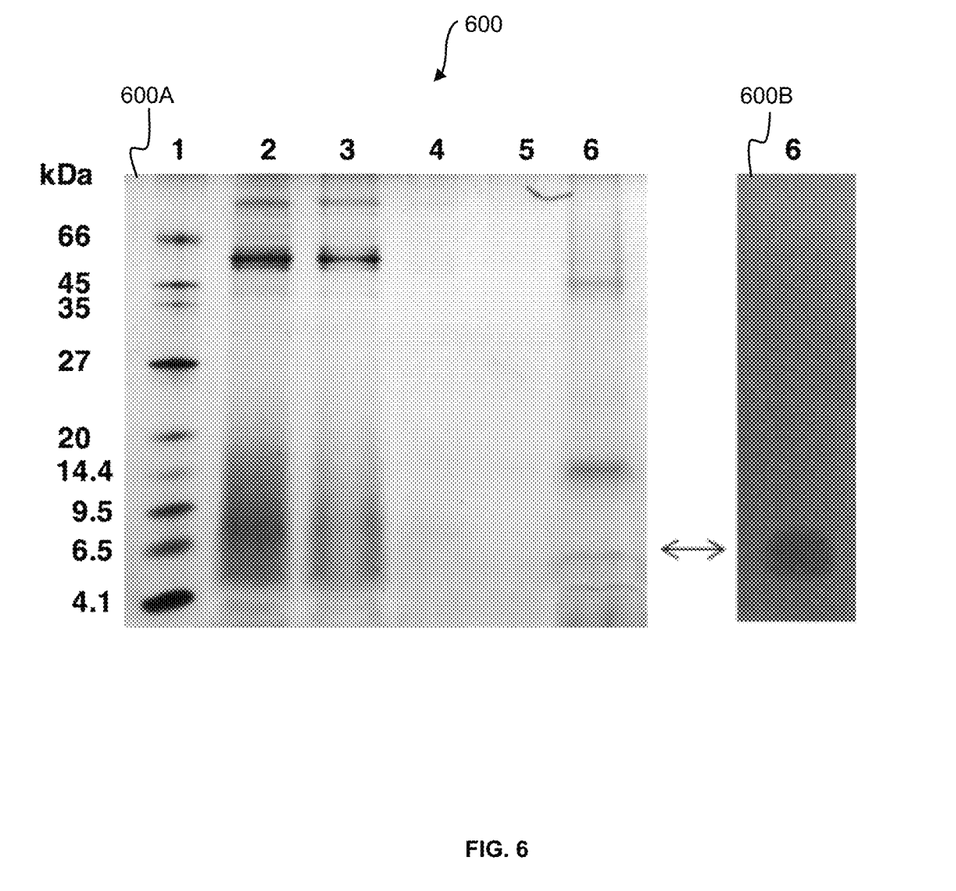
FIG. 6 shows the results of Tricine SDS-PAGE analysis and antimicrobial activity test of pediocin PA-1 purified by hydrophobic interaction chromatography in accordance with an exemplary embodiment of the present invention.

Next referring to FIG. 6, a picture 600A showing the results of Tricine SDS-PAGE analysis and a picture 600B showing antimicrobial activity test of pediocin PA-1 purified by hydrophobic interaction chromatography. Samples are as follows: 1, 4.1-66 kDa Low Range Protein Molecular Weight Marker (Bio Basic Canada Inc.); 2, culture medium of *Pichia pastoris* X33::ped, 3, flow through fraction, 4-6, Elution fraction at 40%, 60% and 100% B, respectively.

Pediocin PA-1 was present in three elution fractions at 40%, 60% and 100% buffer C, corresponding to Ammonium Sulfate concentrations of 0.6, 0.4 and 1.0 M as shown in shown in the picture 600A. The picture 600B shows antibacterial assays which indicated that all fractions had activity against the indicator strain.

Figure 7:
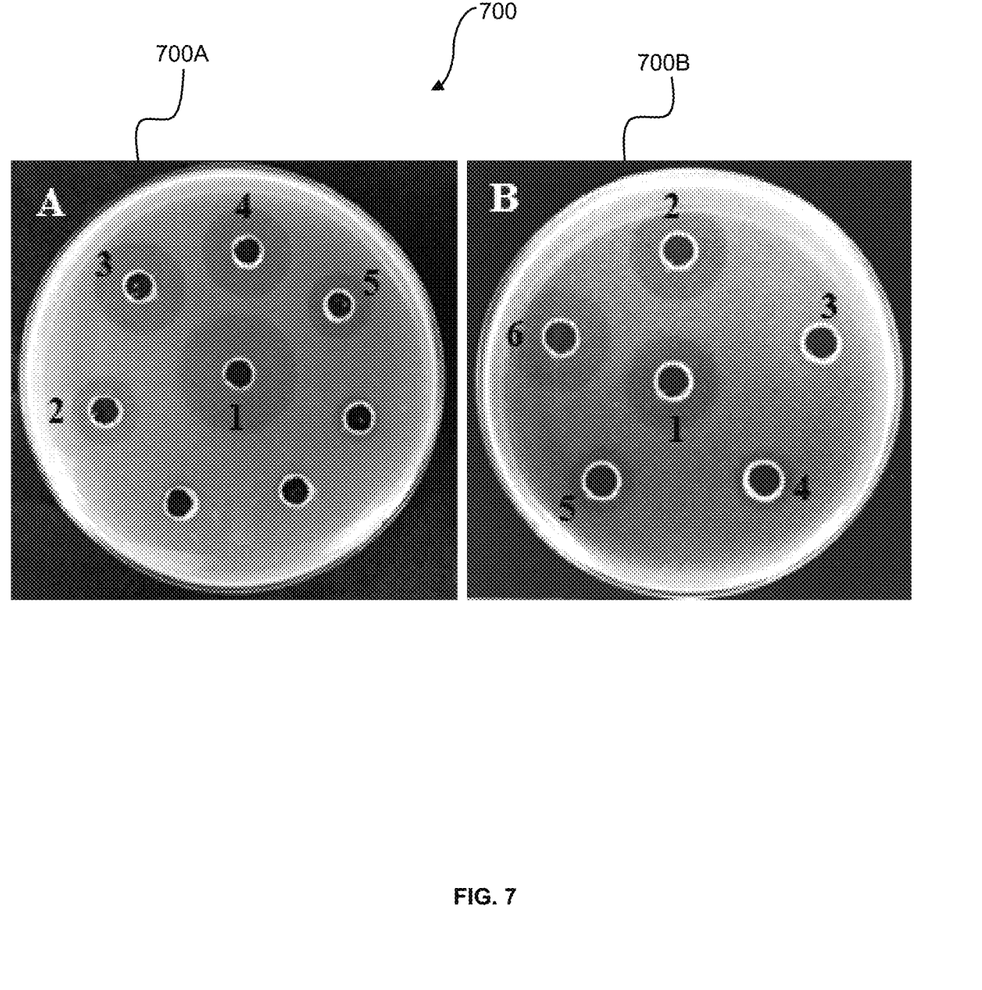
FIG. 7 shows the results of agar diffusion test against *Listeria monocytogenes* ATCC 13932 of pediocin PA-1 purified by cation exchange chromatography (A) and hydrophobic interaction chromatography (B) in accordance with an exemplary embodiment of the present invention.

FIG. 7 illustrates a graph 700A showing the results of agar diffusion test against *Listeria monocytogenes* ATCC 13932 of pediocin PA-1 purified by cation exchange chromatography (A) and a graph 700B showing the results of hydrophobic interaction chromatography (B) in accordance with an exemplary embodiment of the present invention. Samples in FIG. 7A are as follows: 1, 100 μg/ml ampicillin; 2-7, elution fractions at 0.4 M, 0.5 M, 0.6 M, and 0.7 M NaCl, respectively. Samples in FIG. 7B are as follows: 1, ampicillin 50 μg/ml, 2, culture medium of *Pichia pastoris* X33:: ped; 3, wash fraction at 100% A buffer C ($Na_2HPO_4$ 50 mM, $(NH_4)_2SO_4$ 1M, pH 7); 4-6, elution fraction at 40%, 60% and 100% buffer D ($Na_2HPO_4$ 50 mM, pH 7), respectively. The result showed that the elution fraction at 0.5 M NaCl from cation exchange purification and fraction at 100% buffer D from hydrophobic interaction purification yielded strongest antimicrobial activities against *Listeria monocytogenes* with the inhibition zone diameters of 15 mm and 17 mm, respectively.

Example 5: Examining the Characteristics of Recombinant Pediocin PA-1

Figure 8:
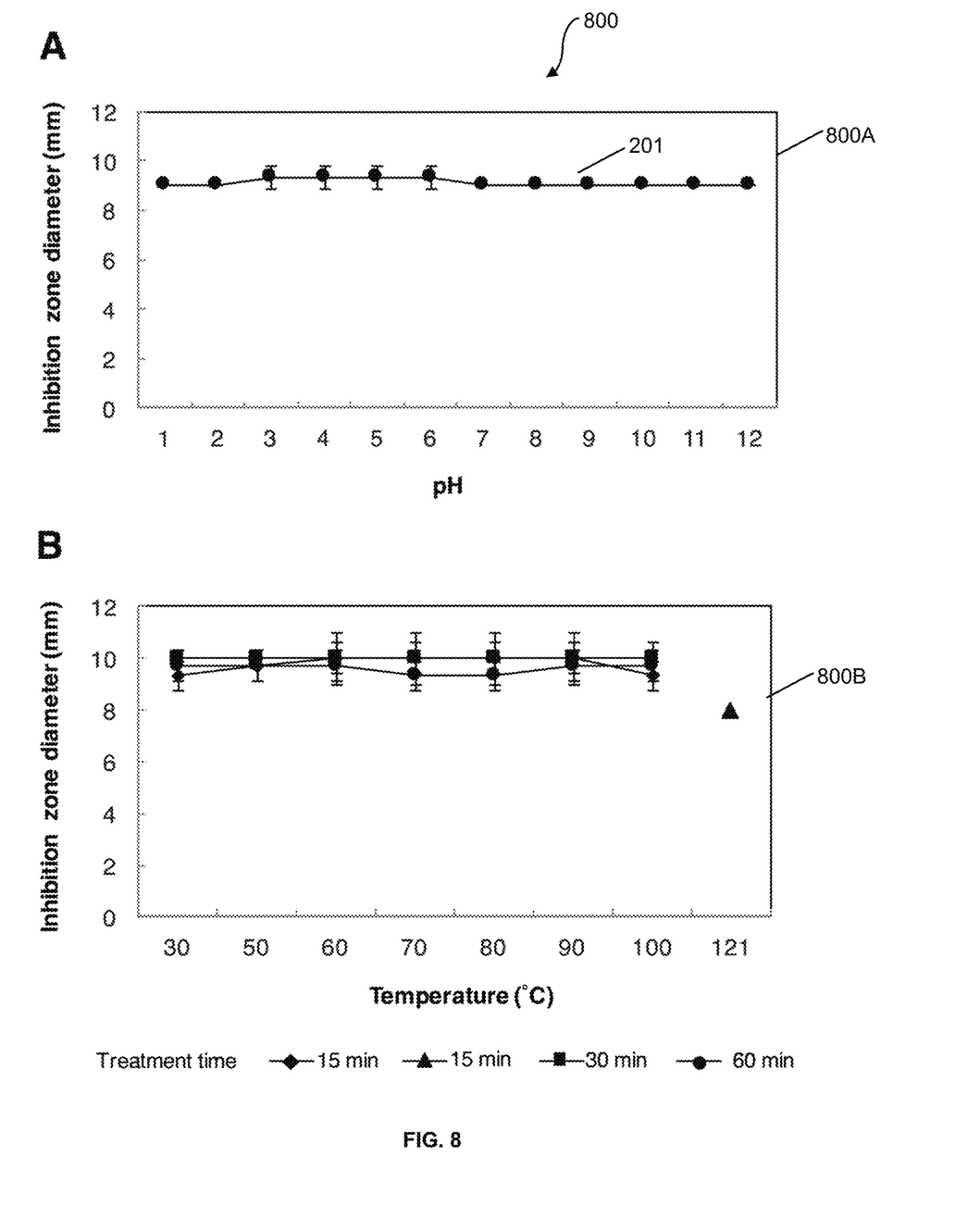
FIG. 8 shows the graphs demonstrating the stability of pediocin PA-1 under extremely high pH (A) and temperature (B) conditions, the antimicrobial activity of pediocin PA-1 being tested using the indicator strain *Listeria monocytogenes* ATCC 13932 in accordance with an exemplary embodiment of the present invention.

Finally referring to FIG. 8 which illustrates graphs 800 indicating the stabilities of pediocin PA-1 obtained by method 200 of the present invention, a graph 800A shows the stability of pediocin PA-1 under extremely high pH (A) and a graph 800B shows the stability of pediocin PA-1 under temperature (B) conditions. The antimicrobial activity of pediocin PA-1 was tested using the indicator strain *Listeria monocytogenes* ATCC 13932.

In one aspect of the present invention, the stability of recombinant pediocin PA-1 under extremely high temperature and pH conditions was studied through antimicrobial assays using the indicator strain *Listeria monocytogenes* ATCC 13932 for its application in food preservation.. As shown in graph 800A, in the pH experiments, the samples containing pediocin PA-1 was adjusted to pH 1.0-12.0 using 1 N HCl solution or 1 N NaOH solution, incubated at 4° C. for 1 hour, then re-adjusted to pH 6.0 and subjected to the antimicrobial assay. The antimicrobial activity of pediocin PA-1 was not significantly changed under all tested conditions, indicating that the recombinant pediocin PA-1 is stable at pH 1 to 12 for at least 1 hour. In addition, the stability of pediocin PA-1 was also examined at 30° C.-100° C. for 15 min, 30 min, and 60 min and at 121° C. for 20 minutes.

Referring now to graph 800B, it has been previously reported that the prior-art pediocin PA-1 was stable at 100° C. for 1 hour but lost all activity after treated at 121° C. for 20 min (Mandal et al., 2014). In the instant invention, pediocin PA-1 obtained from the recombinant *Pichia pastoris* maintained the full activity at 100° C. for at least 1 hour and, importantly, remained 80% activity after being treated at 121° C. for 20 min, suggesting its superior characteristics over the native pediocin PA-1.

Beside *Listeria monocytogenes* ATCC 13932 strain, we also found that the recombinant pediocin PA-1 had antimicrobial activity against some other bacterial strains including *Listeria innocua, Listeria monocytogenes* VSVTCC, *Vibrio parahaemolyticus, Enterococcus faecalis, Streptococcus thermophilus, Lactobacillus plantarum*.

The foregoing description details certain embodiments of the invention. It will be appreciated, however, that no matter how detailed the foregoing appears in text, the invention can be practiced in many ways. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated. The scope of the invention

REFERENCES

1. Barefoot, S. F., and Klaenhammer, T. R. (1983). Detection and activity of lactacin B, a bacteriocin produced by *Lactobacillus acidophilus*. *Applied and Environmental microbiology* 45(6), 1808-1815.
2. Beaulieu, L. (2005). Production, purification et caracterisation de la pediocine PA-1 naturelle et de ses formes recombinantes: Contribution a la mise en evidence d'une nouvelle activite biologique (French and English text).
3. Beaulieu, L., Groleau, D., Miguez, C. B., Jett& J.-F., Aomari, H., and Subirade, M. (2005). Production of pediocin PA-1 in the methylotrophic yeast *Pichia pastoris* reveals unexpected inhibition of its biological activity due to the presence of collagen-like material. *Protein expression and purification* 43(2), 111-125.
4. Bhunia, A. K., Johnson, M., and Ray, B. (1987). Direct detection of an antimicrobial peptide of *Pediococcus acidilactici* in sodium dodecyl sulfate-polyacrylamide gel electrophoresis. *Journal of Industrial Microbiology* 2(5), 319-322.
5. Chen, C., Sebranek, J. G., Dickson, J. S., and Mendonca, A. F. (2005). Combining Pediocin (ALTA™ 2341) with Thermal Pasteurization for Control of *Listeria monocytogenes* on Frankfurters. *Animal Industry Report* 651(1), 62.
6. Grantham, R., Gautier, C., and Gouy, M. (1980). Codon frequencies in 119 individual genes confirm corsistent choices of degenerate bases according to genome type. *Nucleic acids research* 8(9), 1893-1912.
7. Gratia, A., and Fredericq, P. (1946). * DIVERSITE DES SOUCHES ANTIBIOTIQUES DE B-COLI ET ETENDUE VARIABLE DE LEUR CHAMP DACTION. COMPTES RENDUS DES SEANCES DE LA SOCIETE DE BIOLOGIE ET DE SES FILIALES 140(11), 1032-1033.
8. Halami, P. M., and Chandrashekar, A. (2007). Heterologous expression, purification and refolding of an anti-listerial peptide produced by *Pediococcus acidilactici* K7. *Electronic Journal of Biotechnology* 10. doi: 10.2225/vol10-issue4-fulltext-11.
9. Henderson, J. T., Chopko, A. L., and van Wassenaar, P. D. (1992). Purification and primary structure of pediocin PA-1 produced by *Pediococcus acidilactici* PAC-1.0. *Arch Biochem Biophys* 295(1), 5-12.
10. Line, J., Svetoch, E., Eruslanov, B., Perelygin, V., Mitsevich, E., Mitsevich, I., et al. (2008). Isolation and purification of enterocin E-760 with broad antimicrobial activity against gram-positive and gram-negative bacteria. *Antimicrobial agents and chemotherapy* 52(3), 1094-1100.
11. Mandal, B., Chowdhury, R., and Jee, C. B. (2014). Purification and characterization of pediocin produced by *Pediococcus acidilactici* ncim 2292 *International Journal of Pharmacy and Pharmaceutical Science* 6(6), 5.
12. Messaoudi, S., Kergourlay, G., Rossero, A., Ferchichi, M., Prevost, H., Drider, D., et al. (2011). Identification of lactobacilli residing in chicken ceca with antagonism against *Campylobacter*. *International Microbiology* 14(2), 103-110.
13. Moon, G. S., Pyun, Y. R., and Kim, W. J. (2006). Expression and purification of a fusion-typed pediocin PA-1 in *Escherichia coli* and recovery of biologically active pediocin PA-1. *Int J Food Microbiol* 108(1), 136-140. doi: 10.1016/j.ijfoodmicro.2005.10.019.
14. Nakamura, Y., Gojobori, T., and Ikemura, T. (1999). Codon usage tabulated from the international DNA sequence databases; its status 1999. *Nucleic acids research* 27(1), 292-292.
15. Navratilova, P., Vyhnalkova, J., Vorlova, L., and JEŘÁBKOVÁ, J. (2014). A Plate Diffusion Method for Detecting Fluoroquinolone Residues in Raw Cow's Milk. *Czech Journal of Food Science* 32(3).
16. Nazef, L., Belguesmia, Y., Tani, A., Prévost, H., and Drider, D. (2008). Identification of lactic acid bacteria from poultry feces: evidence on anti-*Campylobacter* and anti-*Listeria* activities. *Poultry Science* 87(2), 329-334.
17. Schoeman, H., Vivier, M. A., Du Toit, M., Dicks, L. M., and Pretorius, I. S. (1999). The development of bactericidal yeast strains by expressing the *Pediococcus acidilactici* pediocin gene (pedA) in *Saccharomyces cerevisiae*. *Yeast* 15(8), 647-656. doi: 10.1002/(SICI)1097-0061(19990615)15:8<647::AID-YEA409>3.0.CO;2-5.
18. Sinclair, G., and Choy, F. Y. (2002). Synonymous codon usage bias and the expression of human glucocerebrosidase in the methylotrophic yeast, *Pichia pastoris*. *Protein expression and purification* 26(1), 96-105.
19. Venema, K., Chikindas, M. L., Seegers, J., Haandrikman, A. J., Leenhouts, K. J., Venema, G., et al. (1997). Rapid and efficient purification method for small, hydrophobic, cationic bacteriocins: purification of lactococcin B and pediocin PA-1. *Applied and environmental microbiology* 63(1), 305-309.

should therefore be construed in accordance with the appended claims and any equivalents thereof.

What is claimed is:

1. A codon-optimized nucleotide sequence consisting the nucleic acid sequence set forth in SEQ ID NO: 1.

2. A *Pichia pastoris* yeast X33::ped deposited as NRRL Y-67635, wherein the *Pichia pastoris* yeast X33::ped is transformed with the codon-optimized nucleotide sequence of claim 1 and said nucleotide sequence encodes a pediocin PA-1 protein having antimicrobial activities against a plurality of target bacterial strains.

3. The *Pichia pastoris* yeast X33::ped according to claim 2, wherein the codon-optimized nucleotide sequence is integrated into the *Pichia pastoris* yeast genome at the AOX1 region.

4. The *Pichia pastoris* yeast X33::ped according to claim 2, wherein said plurality of target bacterial strains comprise *Listeria monocytogenes* ATCC 1393, *Pediococcus acidilactici* PAC1.0, *Listeria innocua*, *Vibrio parahaemolyticus*, *Enterococcus faecalis*, *Streptococcus thermophilus*, and *Lactobacillus plantarum*.

5. The *Pichia pastoris* yeast X33::ped according to claim 2, wherein said antimicrobial activities of said pediocin PA-1 protein are fully maintained for at least one hour at 100° C. and at least 20 minutes at 121° C. and stable at pH levels ranging from 1 to 12.

6. A method for producing the *Pichia pastoris* yeast X33::ped of claim 2, comprising:
   (i) designing a codon-optimized nucleotide sequence consisting of the nucleic acid sequence set forth in SEQ ID NO: 1, wherein SEQ ID NO: 1 encodes a pediocin PA-1 protein having antimicrobial activities against a plurality of target bacterial strains;
   (ii) amplifying the nucleic acid sequence set forth in SEQ ID NO: 1 by polymerase chain reaction (PCR) using a pair of oligonucleotide primers;
   (iii) transforming a *Pichia pastoris* yeast X33 strain with the codon-optimized nucleotide sequence set forth in SEQ ID NO: 1 to produce the *Pichia pastoris* yeast X33::ped deposited as NRRL Y-67635;

(iv) growing the *Pichia pastoris* yeast X33::ped in a preset culture medium; and (v) purifying said culture medium to obtain the *Pichia pastoris* yeast X33::ped.

7. The method according to claim 6, wherein said pair of oligonucleotide primers comprise a forward primer XhoIF having the nucleic acid sequence set forth in SEQ ID NO: 2 and a reverse primer NotIR having the nucleic acid sequence set forth in SEQ ID NO: 3.

8. The method of claim 6, wherein said step (iv) further comprises:

growing said *Pichia pastoris* yeast X33::ped in a growth medium at 25-37° C. with agitation and oxygenation until the end of a log phase; and growing said *Pichia pastoris* yeast X33::ped in an inducible medium at 25-37° C. with agitation and oxygenation.

9. The method according to claim 8, wherein said growth medium comprises a carbon source, a nitrogen source, and a salt composition.

10. The method according to claim 9, wherein said carbon source comprises a glycerol.

11. The method according to claim 9, wherein said carbon source comprises a sugar.

12. The method according to claim 9, wherein said nitrogen source comprises a peptone.

13. The method according to claim 9, wherein said nitrogen source comprises a tryptone.

14. The method according to claim 9, wherein said nitrogen source comprises a yeast nitrogen base.

15. The method according to claim 9, wherein said salt composition comprises a potassium (K), a phosphor (P), a Sulfur (S), a Calcium (Ca), a Magnesium (Mg), an Arsenic (As), a Chromium (Cr), a Fluorine (F), an Iodine (I), a Cobalt (Co), a Copper (Cu), a Manganese (Mn), a Molybdenum (Mo), a Selenium (Se), a Vanadium (V), a Zinc (Zn), and a tin (Sn).

16. The method according to claim 6, wherein said antimicrobial activities of said pediocin PA-1 protein are fully maintained for at least one hour at 100° C. and at least 20 minutes at 121° C. and stable at pH levels ranging from 1 to 12.

17. The method according to claim 6, wherein said purifying step further comprises a cation exchange chromatography.

18. The method according to claim 6, wherein the nucleic acid sequence set forth in SEQ ID NO: 1 is amplified by a forward primer AOXF having the nucleic acid sequence set forth in SEQ ID NO: 4 and a reverse primer AOXR having the nucleic acid sequence set forth in SEQ ID NO: 5.

19. The method according to claim 8, wherein said inducible medium further comprises methanol.

* * * * *